(12) United States Patent
Best

(10) Patent No.: US 8,444,340 B2
(45) Date of Patent: May 21, 2013

(54) DENTAL TREATMENT INSTRUMENT

(76) Inventor: Alphonsus Best, Southern Harbour (CA)

( * ) Notice: Subject to any disclaimer, the term of this patent is extended or adjusted under 35 U.S.C. 154(b) by 604 days.

(21) Appl. No.: 12/659,713

(22) Filed: Mar. 18, 2010

(65) Prior Publication Data
US 2011/0225748 A1 Sep. 22, 2011

(51) Int. Cl.
*A46B 9/04* (2006.01)
*A46B 11/00* (2006.01)
*A46B 11/06* (2006.01)
*A47K 7/02* (2006.01)

(52) U.S. Cl.
USPC ........... 401/289; 401/196; 401/201; 401/203; 15/167.1; 132/308

(58) Field of Classification Search
USPC ................. 401/196, 201, 203, 204, 205, 268, 401/270, 282, 283, 289
See application file for complete search history.

(56) References Cited

U.S. PATENT DOCUMENTS

| | | | |
|---|---|---|---|
| 913,184 A | 2/1909 | Alexander | |
| 1,408,520 A | 3/1922 | Larsen | |
| 1,580,799 A | 4/1926 | Anzalone | |
| 3,214,775 A | 11/1965 | Morov et al. | |
| 3,273,189 A | 9/1966 | Levinson et al. | |
| 3,386,439 A | 6/1968 | Harper | |
| 3,422,469 A | 1/1969 | Tunstall et al. | |
| 3,424,156 A * | 1/1969 | Smith | 604/150 |
| 3,487,828 A * | 1/1970 | Troy | 601/162 |
| 3,499,440 A | 3/1970 | Gibbs | |
| 3,509,874 A | 5/1970 | Stillman | |
| 3,593,707 A * | 7/1971 | Pifer | 601/163 |
| 3,610,234 A * | 10/1971 | Oates | 601/155 |
| 3,973,558 A | 8/1976 | Stouffer et al. | |
| 4,122,983 A * | 10/1978 | Jolly | 222/390 |
| 4,175,879 A | 11/1979 | Molinari | |
| 4,303,064 A | 12/1981 | Buffa | |
| 4,456,222 A | 6/1984 | Shen | |
| 4,643,460 A | 2/1987 | Lieberg | |
| 4,672,953 A | 6/1987 | DiVito | |
| 4,743,199 A | 5/1988 | Weber et al. | |
| 4,928,675 A | 5/1990 | Thornton | |
| 4,941,459 A | 7/1990 | Mathur | |
| 5,194,156 A | 3/1993 | Tomchak | |
| 5,231,978 A | 8/1993 | Kao et al. | |
| 5,304,010 A | 4/1994 | Hsing-San | |
| 5,711,759 A | 1/1998 | Smith et al. | |
| 5,746,595 A | 5/1998 | Ford | |
| 5,876,135 A * | 3/1999 | Wang et al. | 401/46 |
| 6,371,674 B1 | 4/2002 | Lerner | |
| 7,390,026 B2 | 6/2008 | Noda | |
| 2004/0045107 A1 | 3/2004 | Egeresi | |

* cited by examiner

*Primary Examiner* — David Walczak
*Assistant Examiner* — Joshua Wiljanen
(74) *Attorney, Agent, or Firm* — Mario Theriault

(57) ABSTRACT

The dental treatment instrument includes a toothbrush having common brush head dimensions and a nozzle on the backside of the bristle pad thereof. The tip of the nozzle points backward relative to the bristle pad and is inclined away from the handle end of the toothbrush. The bristle pad is used as a rest pad laid against the cheek wall of the user for steadying the movement of the nozzle. In another aspect of the present invention, the toothbrush has a push-button-operated valve mounted in the handle end of the toothbrush for selectively letting water flow through to the nozzle. The push button is partly enclosed in a shroud. The push button is mounted in the shroud with a sliding fit. The shroud prevents water and toothpaste from seeping below the push-button.

2 Claims, 2 Drawing Sheets

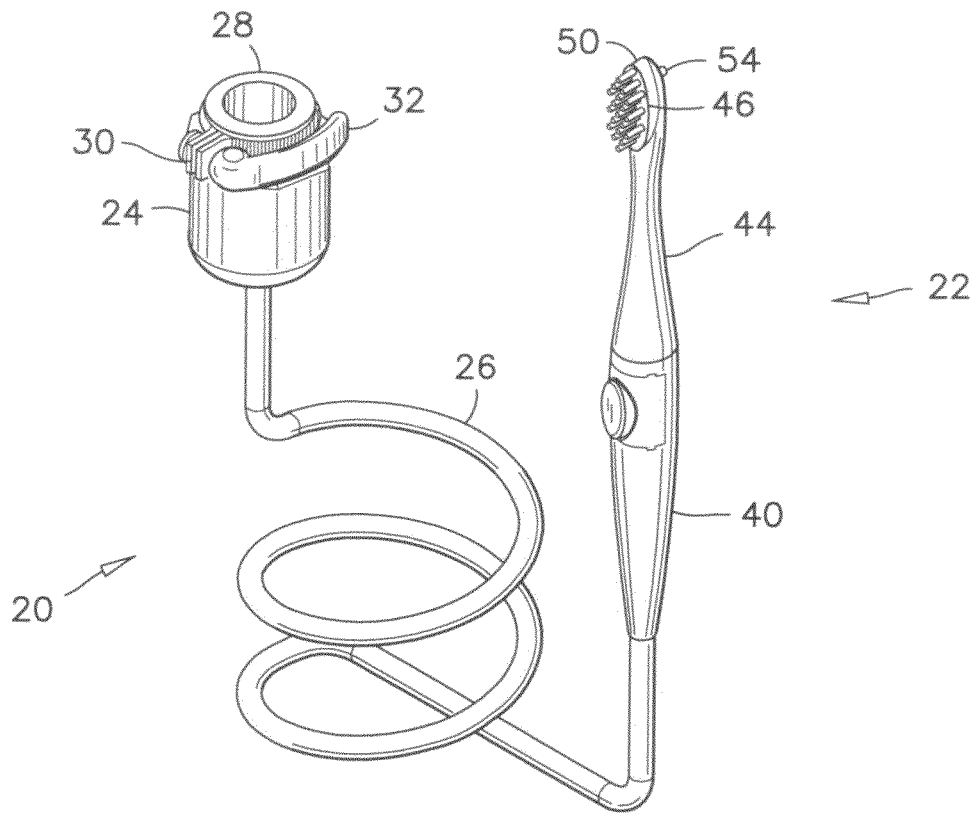
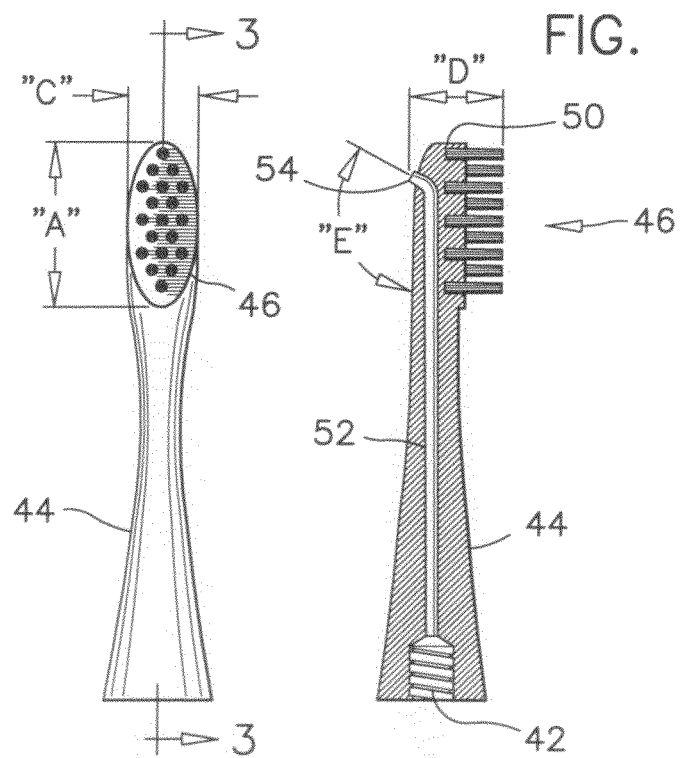
FIG. 1
FIG. 2    FIG. 3

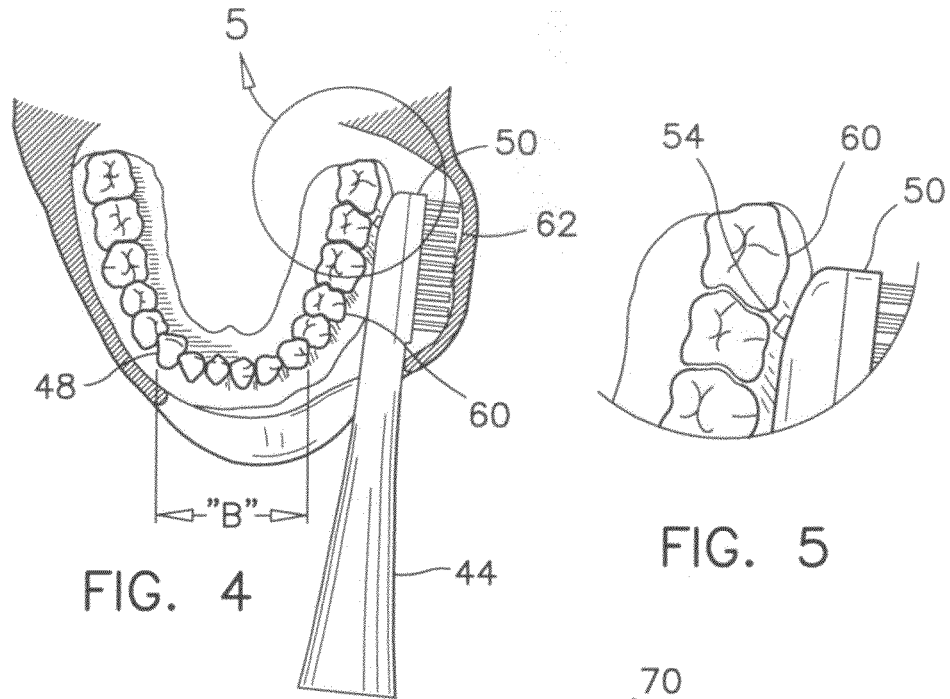
FIG. 4
FIG. 5
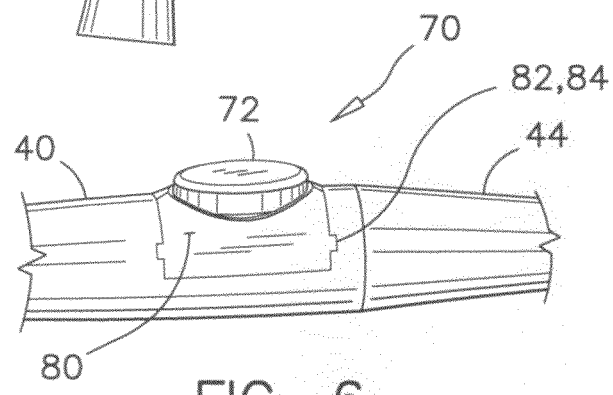
FIG. 6
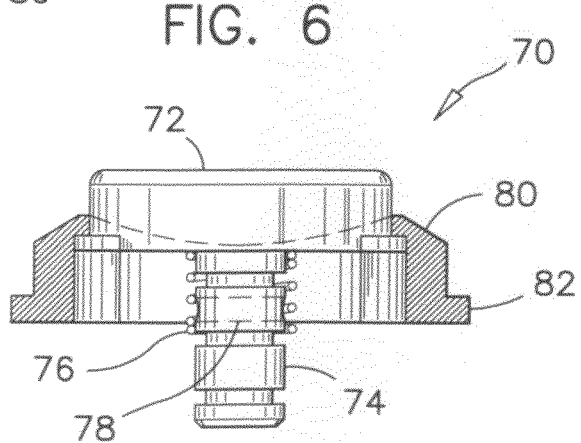
FIG. 7

DENTAL TREATMENT INSTRUMENT

FIELD OF THE INVENTION

This invention pertains to instruments for brushing and washing teeth, and more particularly, it pertains to a common-size toothbrush having a water conduit and a spray nozzle incorporated therein.

BACKGROUND OF THE INVENTION

Common dimensions of toothbrushes have evolved from designers' experiences and from users' feedback during many generations. Toothbrushes having common dimensions are comfortable for brushing teeth of adults and children. A toothbrush having common dimensions fits easily and comfortably along the gums and under the tongue of the user, and it is efficient in brushing several teeth at the time. These dimensions constitute a mature subject matter wherein improvements are now rare. Therefore, it is believed that any innovation in toothbrushes should respect the importance of maintaining these common dimensions.

Water jets have also been proven to be efficient in rinsing one's teeth and mouth. Several attempts have been made in the past to incorporate a water conduit and a nozzle in a toothbrush, but generally this has been done to the detriment of maintaining ideal toothbrush dimensions.

It is believed that the toothbrushes of the prior art having a water jet incorporated therein are difficult to introduce in the mouth; they cannot be brought close to the gum line for treating the gums for example, and they are unstable inside the mouth of the user. These inconveniences will be better appreciated when understanding the structural differences in the dental treatment instrument described herein.

Examples of toothbrush and water jet combinations of the prior art are numerous and include the devices described in the following documents:
U.S. Pat. No. 913,184 issued to C. L. Alexander on Feb. 23, 1909;
U.S. Pat. No. 1,408,520 issued to O. H. Larsen on Mar. 7, 1922;
U.S. Pat. No. 1,580,799 issued to R. Anzalone on Apr. 13, 1926;
U.S. Pat. No. 3,214,775 issued to I. I. Murov et al., on Nov. 2, 1965;
U.S. Pat. No. 3,273,189 issued to L. E. Levinson et al., on Sep. 20, 1966;
U.S. Pat. No. 3,509,874 issued to T. Stillman on May 5, 1970;
U.S. Pat. No. 3,593,707 issued to G. W. Pifer on Jul. 20, 1971;
U.S. Pat. No. 4,175,879 issued to P. Molinari on Nov. 27, 1979;
U.S. Pat. No. 4,303,064 issued to M. J. Buffa on Dec. 1, 1981;
U.S. Pat. No. 4,743,199 issued to A. Weber et al., on May 10, 1988;
U.S. Pat. No. 4,928,675 issued to T. F. Thornton on May 29, 1990;
U.S. Pat. No. 5,304,010 issued to C. Hsing-San on Apr. 19, 1994;
U.S. Pat. No. 5,746,595 issued to F. E. Ford on May 5, 1998;
U.S. Pat. No. 5,876,135 issued to Y. J. Wang et al., on Mar. 2, 1999;
US Patent Appl. 2004/0045107 filed by Z. Egeresi on Mar. 11, 2004;

The documents of the prior art that are listed above generally disclose toothbrushes having water jets pointing amongst the bristles of the toothbrush; toward the far end of the bristle pad, or at right angle backward relative to the bristle pad. It is believed that these arrangements are inconvenient for holding the nozzle of the water jets close to a dental region to be irrigated for example.

The water jets that are of interest herein pertain to dental and mouth treatment. These jets can be used to clean gaps between the teeth as an alternative to flossing for example, or to massage the gums. Also, the water pumped through these jets may contain a solution such as mouthwash, fluoride, baking soda, salt, a healing product, or other solutions recommended by dentists to reduce plaque; to disinfect the gums; or to alleviate the pain of a toothache.

During these treatments, it is important to be able to hold the water spray steady pointing against a specific region in the mouth of the user. The efficiency of these treatments depends on the stability and precision with which the user can hold the water spray pointing at the region to be treated. In that respect, dislodging food particles from between the teeth is good image to appreciate such requirement of stability and precision in treating one's teeth.

The prior art also contains dental irrigation instruments that are used to maintain dental hygiene basically. Examples of these instruments are described in the following documents:
U.S. Pat. No. 3,386,439 issued to T. P. Harper on Jun. 4, 1968;
U.S. Pat. No. 3,499,440 issued to A. Gibbs on Mar. 10, 1970;
U.S. Pat. No. 3,973,558 issued to R. D. Stouffer et al., on Aug. 10, 1976;
U.S. Pat. No. 4,672,953 issued to E. E. DiVito on Jun. 16, 1987;
U.S. Pat. No. 4,941,459 issued to S. K. Mathur on Jul. 17, 1990;
U.S. Pat. No. 5,231,978 issued to T. Kao et al., on Aug. 3, 1993.

These spray nozzles are held in one's hand with the tip inserted in the mouth. The precision of these water jets depends on how steady one can hold the nozzle in his/her hand, while standing in front of a mirror for example. It is believe that these instruments are better used by a second person such as a dentist for example, who can rest his/her hand on the patient's chin, while steadying the patient's head with the other hand. This image illustrates the difficulties in using water jet instruments and it will be better understood if one can visualize that the user of the instrument could be a child or a person having less dexterity than others.

Therefore it is believed that there is a market need for a toothbrush and water jet combination which is easy to hold steady in one's mouth, and which is movable with precision in one's mouth.

SUMMARY OF THE INVENTION

In the present invention, however, there is provided a dental treatment instrument that has common brush head dimensions and a nozzle on the backside of the bristle pad thereof. The bristle pad is used as a rest surface laid against the cheek wall of the user for steadying the movement of the nozzle.

In one aspect of the present invention, there is provided a dental treatment instrument comprising a toothbrush having a handle section; a brush head and a water conduit passing there through from the handle end to the brush head. The water conduit is connected to a source of water under pressure.

The brush head has a bristle pad thereon and a nozzle connected to the water conduit. The brush head has common brush head dimensions and the nozzle has a tip that is located within a length of the bristle pad. The tip of the nozzle points backward relative to the bristle pad along a inclination relative to a longitudinal axis of the toothbrush away from the handle end.

This instrument is particularly efficient for resting or for moving the tip of the nozzle in a precise manner along the gum line of the user for applying a treatment solution to the gum line. During this process, the bristle pad is in contact with the cheek wall of the user and helps to stabilize the movement of the toothbrush inside the mouth without requiring an outstanding dexterity by the user.

In another aspect of the present invention, the toothbrush has a push-button-operated valve mounted in the handle end of the toothbrush for selectively letting water flow through the water conduit. The push button is partly enclosed in a shroud. The push button is mounted in the shroud with a sliding fit and is urged outward relative to the handle end by a spring.

The shroud prevents water and toothpaste from seeping below the push-button for preventing corrosion of the spring and soiling of the valve stem.

This brief summary has been provided so that the nature of the invention may be understood quickly. A more complete understanding of the invention can be obtained by reference to the following detailed description of the preferred embodiment thereof in connection with the attached drawings.

BRIEF DESCRIPTION OF THE DRAWINGS

One embodiment of the present invention is illustrated in the accompanying drawings, in which like numerals denote like parts throughout the several views, and in which:

FIG. 1 is a perspective view of the preferred dental treatment instrument;

FIG. 2 is a face view of the head section of the toothbrush in the preferred dental treatment instrument;

FIG. 3 is a cross-section view of the head section of the toothbrush, as seen along section line 3-3 in FIG. 2;

FIG. 4 is a plan view of a lower teeth of a user, showing a preferred positioning the head section of the toothbrush when directing a water jet at the gum line of the user;

FIG. 5 is an enlarged view of the nozzle tip in the preferred dental treatment instrument as seen in detail circle 5 in FIG. 4;

FIG. 6 is a perspective view of the thumb-operated valve on the toothbrush of the preferred dental treatment instrument;

FIG. 7 is a partial cross-section view of the thumb-operated valve shown in FIG. 6.

DESCRIPTION OF THE PREFERRED EMBODIMENT

While this invention is susceptible of embodiment in many different forms, there is shown in the drawings and will be described in details herein one specific embodiment of a dental treatment instrument.

The present disclosure is to be considered as an example of the principles of the invention and is not intended to limit the invention to the embodiment illustrated and described.

Referring firstly to FIG. 1, the preferred dental treatment instrument 20 comprises broadly a toothbrush 22, a faucet adapter 24 and a hose 26 extending between the faucet adapter 24 and the toothbrush 22.

The faucet adapter 24 has a cylindrical shape and a hollow cavity therein to receive a filter media, and/or dissolvable tablets of mouthwash, disinfectant or medicinal media. The water passing though the faucet adapter 24 is thereby free of impurities or/and it is treated to provide a therapeutic effect in the mouth of the user.

The faucet adapter 24 has a rubber sleeve 28 therein that is fitted over the spout of a faucet (not shown). The faucet adapter 24 has a clamp 30 for tightening the sleeve 28 over the spout of the faucet. The clamp 30 is preferably operated by a cam-lock lever 32 so that it is easy to operate with wet hands and by people of all ages.

Referring simultaneously to FIGS. 1-3, the preferred toothbrush 22 is made of two sections. The handle section 40 has a nipple, not shown, at one end thereof to connect the hose 26 thereto, and a threaded stem, not shown, at the other end to connect the handle section 40 to a threaded socket 42 in the end of the head section 44.

The head section 44 has a bristle pad 46 having common brush head dimensions. These dimensions are referred to as common brush head dimensions because that are found on common toothbrushes of many makes and styles. For reference purposes, common brush head dimensions are defined as follows.

The bristle pad 46 has a length "A" that is substantially the same as or slightly more than the distance between the lower cuspid teeth 48, of an adult person, as shown as "B" in FIG. 4. The width of the bristle pad 46 as shown as "C" in FIG. 2 is about 50% or slightly less than the length "A". The thickness of the brush head 50 as shown by dimension "D" in FIG. 3 is about between 55% and 60% of the length "A" of the bristle pad 46.

Referring specifically to FIG. 3, the head section 44 also has a conduit 52 incorporated therein. This conduit 52 is incorporated in the brush head 50 in a way that does not increase the thickness "D" of the brush head 50 beyond that of the common dimensions. The conduit 52 has a nozzle tip 54 pointing backward relative to the bristle pad 46 at an angle "E" of about 120° from the longitudinal axis thereof. The nozzle tip 54 is located within the span 'A' of the bristle pad 46, near the far end of the bristle pad 46.

The conduit 52 is made of a rigid plastic or metal and it is incorporated into the mold of the toothbrush prior to injecting a second type of plastic in the mold for molding the toothbrush 22.

The angle 'E' of 120° has been found to be particularly convenient for holding the nozzle tip 54 in an effective orientation, for rinsing the front teeth for example, without having to place one's hand close to one's ear.

Referring now to FIGS. 4 and 5, the advantages in the stability of toothbrush will be explained. This explanation is given in the context of a user of the preferred toothbrush 22 giving himself/herself a treatment for plaque for example, by holding the nozzle tip 54 of the water jet along the gum line 60, and by moving the nozzle tip 54 slowly along the gum line 60.

Because of the common dimensions of the brush head 50, as mentioned before, the brush head 50 fits comfortably between the teeth and the cheek wall 62 of the user. Also because of the common dimensions of the bristle pad 46, the bristle pad 46 is held steady against the cheek wall 62 of the user and can be moved back and forth in a relatively straight line to keep the nozzle tip 54 pointing against the gum line 60.

It will be appreciated that this movement of the brush head 50 along the gum line 60 is more steady than a same effort using a rotatable brush head or using a toothbrush having a nozzle tip that is located outside the span of the bristle head. It will also be appreciated that a spray of a therapeutic solution that is applied directly at the gum line 60 using the preferred toothbrush 22 is more efficient because the nozzle tip 54 can be brought in direct contact with the gum line 60. The bristle pad 46 is pointing away from the nozzle tip 54 and therefore it provides a steady rest that is secured against the cheek wall 62, thereby requiring less dexterity by the user of the toothbrush 22.

Referring to FIGS. 6 and 7, another structural feature of the preferred toothbrush 22 will be explained. The preferred toothbrush 22 has a button-operated valve 70 to control the flow of water through the conduit 52. This valve 70 has a relatively large oval-shaped button 72, a valve stem 74 and a spring 76 below the button 72, which is shown in a cross-section view, for urging the button 72 outward relative to the handle end 40. The valve stem 74 is only partly illustrated. It will be appreciated by those skilled in the art that three o-rings have not been shown for clarity, and that the dashed-lines at 78 in the upper boss represent a water passage extending through that boss.

The valve 70 is opened by pressing the button 72 down. The operation of the valve is not described further herein because it is not the focus of the present invention.

The feature that is of interest herein is the shroud 80 enclosing the button 72. This shroud 80 has an oval-shaped opening to receive the push button 72 with a sliding fit. The shroud 80 prevents water and toothpaste from accumulating in the spring compartment beneath the button 72, which could cause the spring 76 to corrode. The shroud 80 also prevents the push button 72 from being forced sideways, which could cause water and toothpaste to seep along the valve stem 74 and gradually abrade the valve stem 74 or the barrel, not shown, in which the valve stem 74 moves.

The shroud 80 is secured to the handle portion 40 of the preferred toothbrush by two lips 82 engaged in two corresponding grooves 84 in the handle portion 40. It is believed that the shroud 80 will prevent a premature failure of the button-operated valve 70.

As to other manner of construction, usage and operation of the present invention, the same should be apparent from the above description and accompanying drawings, and accordingly further discussion relative to these aspects of the invention would be considered repetitious and is not provided.

While a single embodiment of a dental treatment instrument has been illustrated and described herein above, it will be appreciated by those skilled in the art that various modifications, alternate constructions and equivalents may be employed without departing from the true spirit and scope of the invention. Therefore, the above description and the illustrations should not be construed as limiting the scope of the invention which is defined by the appended claims.

What is claimed is:

1. A dental treatment instrument comprising a toothbrush having an elongated handle section; a brush head; a bristle pad on said brush head, and a water conduit passing there through from said handle section to said brush head;

said brush head having a tapering backside portion on the end thereof;

said water conduit having means for connection to a source of water under pressure exterior of said handle section;

said brush head having a nozzle thereon extending backward through a backside surface thereof directly opposite from said bristle pad; said nozzle being connected to said water conduit;

said nozzle having a protruding tip located in said tapering backside portion; and pointing endways along an inclination relative to a longitudinal axis of said handle section.

2. The dental treatment instrument as claimed in claim 1 wherein said inclination is an angle of 120° from said longitudinal axis of said handle section.

\* \* \* \* \*